United States Patent [19]

Yoshida et al.

[11] 4,378,992

[45] Apr. 5, 1983

[54] UREA DERIVATIVES, AND THEIR PRODUCTION AND USE

[75] Inventors: Ryo Yoshida, Kawanishi; Ichiki Takemoto, Takarazuka; Seizo Sumida, Nishinomiya; Katsuzo Kamoshita, Osaka, all of Japan

[73] Assignee: Sumitomo Chemical Company, Limited, Osaka, Japan

[21] Appl. No.: 114,746

[22] Filed: Jan. 24, 1980

[30] Foreign Application Priority Data

Jan. 30, 1979 [JP] Japan .................................. 54-9944

[51] Int. Cl.³ ...................... A01N 47/30; C07C 69/76; C07C 127/19
[52] U.S. Cl. .......................................... 71/120; 71/98; 260/453 RW; 564/49; 564/52
[58] Field of Search .................... 260/453; 71/98, 120; 564/49, 52

[56] References Cited

U.S. PATENT DOCUMENTS

| | | | |
|---|---|---|---|
| 4,123,256 | 10/1978 | Yoshida et al. | 71/105 |
| 4,149,874 | 4/1979 | Felix | 71/118 |

FOREIGN PATENT DOCUMENTS

| | | |
|---|---|---|
| 868406 | 6/1978 | Belgium . |
| 871568 | 10/1978 | Belgium . |
| 2045064 | 3/1971 | France . |
| 54-9246 | 1/1979 | Japan . |
| 1055741 | 7/1967 | United Kingdom . |
| 2013669 | 11/1979 | United Kingdom . |

OTHER PUBLICATIONS

Chemical Abstracts, vol. 87, No. 19, 7th Nov. 1977, p. 559, No. 151868m.

Chemical Abstracts, vol. 73, No. 15, 12th Oct. 1970, p. 263, No. 75986s.

*Primary Examiner*—Catherine L. Mills
*Attorney, Agent, or Firm*—Birch, Stewart, Kolasch & Birch

[57] ABSTRACT

Novel N'-phenyl-N-methylurea derivatives of the formula:

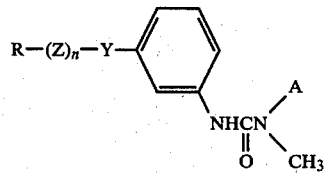

wherein R is a $C_4$–$C_{10}$ cycloalkyl group, a $C_4$–$C_{10}$ cycloalkenyl group, a $C_4$–$C_{10}$ cycloalkyl group condensed with a benzene ring or substituted with at least one $C_1$–$C_4$ alkyl group or a $C_4$–$C_{10}$ cycloalkenyl group condensed with a benzene ring or substituted with a $C_1$–$C_4$ alkyl group, Z is a $C_1$–$C_4$ alkylene group which may have an atom of oxygen and/or sulfur at the terminal of and/or inside the carbon chain, Y is an oxygen atom or a sulfur atom, A is a hydrogen atom, a methyl group or a methoxy group and n is an integer of 0 or 1 with the proviso that in the chain consisting of —(Z-)$_n$—Y—, oxygen and/or sulfur atoms can not be present in succession, which shows a pronounced herbicidal activity against a wide variety of weeds in the cultivation of crop plants without any material toxicity to mammals and any chemical injury to said crop plants.

11 Claims, No Drawings

UREA DERIVATIVES, AND THEIR PRODUCTION AND USE

The present invention relates to N'-phenyl-N-methylurea derivatives of the formula:

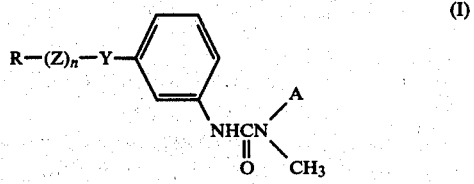

wherein R is a $C_4$-$C_{10}$ cycloalkyl group, a $C_4$-$C_{10}$ cycloalkenyl group, a $C_4$-$C_{10}$ cycloalkyl group condensed with a benzene ring or substituted with at least one $C_1$-$C_4$ alkyl group or a $C_4$-$C_{10}$ cycloalkenyl group condensed with a benzene ring or substituted with a $C_1$-$C_4$ alkyl group, Z is a $C_1$-$C_4$ alkylene group which may have an atom of oxygen and/or sulfur at the terminal of and/or inside the carbon chain, Y is an oxygen atom or a sulfur atom, A is a hydrogen atom, a methyl group or a methoxy group and n is an integer of 0 or 1 with the proviso that in the chain consisting of —(Z-)$_n$—Y—, oxygen and/or sulfur atoms can not be present in succession, and their production and use.

Thus, R in the formula (I) can represent a cyclic hydrocarbon ring such as cyclobutane, cyclopentane, cyclohexane, cycloheptane, cyclooctane, cyclononane, cyclodecane, adamantane, bicyclo(2.2.1)heptane, tricyclo(5.2.1.0)decane, cyclohexene, indane or tetralin.

Rice plant, wheat, corn, soybean, cotton and sugarbeet and the like are crops of world-wide importance and, in the cultivation of these crops, chemical control of weeds is necessary to prevent reductions in the yield.

Among substituted urea derivatives, as is well known, there are compounds having a strong herbicidal activity, such as N'-4-chlorophenyl-N,N-dimethylurea (monuron) and N'-3,4-dichlorophenyl-N,N-dimethylurea (diuron). It is also well known that the herbicidal activity of these urea derivatives is due to the inhibition of photosynthesis. Photosynthesis is a physiological function peculiar to higher plants and does not take place in mammals. Accordingly, specific inhibitors of the photosynthetic process usually cause no significant harm to mammals but can be extremely effective in the extermination of higher plants. In fact, herbicidal photosynthesis inhibitors such as monuron, diuron, 5-bromo-3-sec-butyluracil (bromacil) and the like are all low in mammalian toxicity. However, they exert a herbicidal activity against all higher plants, i.e. crops and weeds alike, since photosynthesis is common to all of the higher plants. Thus, most photosynthesis inhibitors are non-selective and damage crop plants.

For a compound to be a selective herbicide, it has to have both a strong herbicidal activity against weeds and a high level of selectivity to the intended crop. However, such selective herbicides are very difficult to find and can not easily be predicted by mere analogy and modification of known chemical structures. Therefore, a highly detailed study with trial and error is necessary to find such selective herbicides. For example, N'-3,4-dichlorophenyl-N-methoxy-N-methylurea (linuron) among urea series compounds has selectivity to Umbelliferae family plants, but compounds having a methyl or ethyl group in place of the methoxy group of linuron lose the selectivity to the same plants completely [Herbicide Handbook of The Weed Science Society of America, 3rd Ed., pages 172–176 and 221–225 (1974)]. As described above, the mechanism of the selective herbicidal activity is very specific, and a slight difference in chemical structure results in a large difference in degree and kind of selectivity.

Attention was paid to urea series compounds from the standpoints of low toxicity to mammals and strong herbicidal activity, and attempt was made to produce the derivatives improved in selectivity. As the result, it has now been found that the N'-phenyl-N-methylurea derivatives of the formula (I) exhibit a strongly herbicidal activity against many weeds by post-emergence treatment, and at the same time show no material chemical injury to important crop plants. It is also found that they have a high selectivity to rice plants without any phytotoxicity when used as herbicides on paddy rice test.

Referring to the herbicidal activity of the N'-phenyl-N-methylurea derivatives of the formula (I) in more detail, they have a strong herbicidal activity against a wide range of paddy field weeds by either pre-emergence treatment or post-emergence treatment. For example, they have a strong herbicidal activity against paddy field weeds such as toothcup (*Rotala indica*), water starwort (*Callitriche verna*), false pimpernel (*Lindernia pyxidaria*), pickerel weed (*Monochoria vaginalis*), *Dopatrium junceum, Vandellia angustifolia*, barnyard grass (*Echinochloa crusgalli*), nutsedge sp. (*Cyperus difformis*), hardstem bulrush (*Scirpus acutus*) and the like. But, they have a high selectivity to rice plants as described above. Also, the compounds (I) have a strong herbicidal activity against a wide range of upland field weeds when applied by post-emergence treatment. The field weeds include, for example, broad-leaved weeds such as cocklebur (*Xanthium pennsylvanicum*), sunflower (*Helianthus annuus*), redroot pigweed (*Amaranthus retroflexus*), common lambsquarters (*Chenopodium album*), tall morningglory (*Ipomoea purpurea*), jimsonweed (*Datura stramonium*), black nightshade (*Solanum nigrum*), prickly sida (*Sida spinosa*), sicklepod (*Cassia obtusifolia*), common purslane (*Portulaca oleracea*), smartweed sp. (Poligonum sp.), giant ragweed (*Ambrosia trifida*), velvetleaf (*Abutilon theophrasti*), shepherdspurse (*Capsella bursa-pastoris*), bitter cress sp. (*Cardamine flexuosa*), chickweed (*Stellaria media*), catchweed bedstraw (*Galium aparine*), mouseear chickweed (*Cerastium glomeratum*), *Sagina japonica*, johnson grass (*Sorghum halepense*), hemp sesbania (*Sesbania exaltata*) and the like; and grassy weeds such as barnyard grass (*Echinochloa crusgalli*), large crabgrass (*Digitaria sanguinalis*), green foxtail (*Setaria viridis*, annual bluegrass (*Poa annua*), wild oat (*Avena fatua*) and the like. As described hereinafter, the compounds (I) have a high selectivity to soybean, cotton, sugarbeet, corn and wheat.

The N'-phenyl-N-methylurea derivatives of the formula (I) are novel ones, and N'-(3-benzyloxyphenyl)-N,N-dimethylurea in U.S. Pat. No. 3,819,697 (hereinafter referred to as "control compound (a)") is known to be similar in chemical structure to them. But, the herbicidal activity of the compounds (I) is extremely stronger than that of the control compound (a). That is to say, the herbicidal activity is remarkably improved by replacing the benzyloxy group in the control compound (a) by a substituent such as cycloalkyloxy, cycloalkenyloxy, cycloalkylalkoxy or cycloalkenylalkoxy.

Further, depending on the kind of the cyclic hydrocarbon ring represented by R, the compounds (I) produce a notable selectivity to sugarbeet, which is never seen on the said control compound (a). It is a predominent characteristics that the compounds (I) exhibit the high selectivity to sugarbeet, particularly, by post-emergence treatment (cf. Example B). For instance, N'-3-[2-(1-adamantane)ethoxy]-phenyl-N-methoxy-N-methylurea (Compound No. 19), N'-3-[3(or 4)-(trichloro[5.2.1.0$^{2,6}$]decyl)methoxy]phenyl-N-methoxy-N-methylurea (Compound No. 28), N'-3-[2-(3-methylcyclohexyl)-ethoxy]phenyl-N,N-dimethylurea (Compound No. 38), N'-3-(cyclohexylmethoxy)phenyl-N-methoxy-N-methylurea (Compound No. 5) and N'-3-[3-(cyclopentyl)propoxy]phenyl-N,N-dimethylurea (Compound No. 24) can exterminate weeds without causing any phytotoxicity on sugarbeet by post-emergence application.

Furthermore, the compounds (I) show a high selectivity to soybean, cotton, corn, wheat and rice plant.

The above advantageous properties of the N'-phenyl-N-methylurea derivatives of the formula (I) may be considered to be attributed to the following structural characteristics: (1) the possession of a certain cyclic hydrocarbon ring as a modifying group; and (2) the presence of the urea residue at the m-position to such modifying group.

As stated above, it is clear that the compounds (I) of the present invention are very effective as selective herbicides for agricultural lands. Also, they are excellent herbicides which can be applied in non-crop lands because of their strong herbicidal activity.

The N'-phenyl-N-methylurea derivatives of the formula (I) can be produced by the following methods:

(a) A process comprising reaction of a phenylisocyanate derivative of the formula:

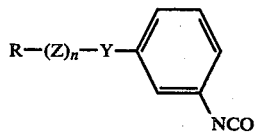

(II)

wherein R, Y, Z and n are each as defined above, with monomethylamine, dimethylamine or N,O-dimethylhydroxylamine.

This reaction may be carried out by treating the phenylisocyanate derivative (II) with monomethylamine, dimethylamine or N,O-dimethylhydroxylamine in a molar proportion of 1:1-3 in the presence of an organic solvent (e.g. benzene, toluene, xylene, diethyl ether, tetrahydrofuran, dioxane, N,N-dimethylformamide, chloroform, carbon tetrachloride), water or a mixture thereof, usually at a temperature of 0° to 50° C. for a period of time from an instant to 10 hours.

(b) A process comprising methylation of an N'-phenyl-N-hydroxyurea derivative of the formula:

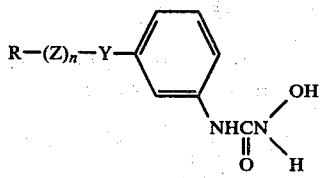

(III)

wherein R, Y, Z and n are each as defined above.

As the methylating agent, there may be used, for example, methyl iodide, dimethyl sulfate or diazomethane in an amount of 2.0–2.5 mol to 1 mol of the N'-phenyl-N-hydroxyurea derivative (III). When dimethyl sulfate is used, for example, the reaction can be carried out in an organic solvent (e.g. benzene, toluene, xylene, methanol, ethanol, isopropanol, diethyl ether, tetrahydrofuran, dioxane, methylene chloride), water and a mixture thereof in the presence of an alkali (sodium hydroxide, potassium hydroxide) in an amount of 2–2.5 mol to 1 mol of the N'-phenyl-N-hydroxyurea derivative (III). The existence of a phase transfer catalyst such as a quaternary ammonium salt in an amount of 0.1–10 mol % based on the N'-phenyl-N-hydroxyurea derivative (III) is advantageous in the reaction. The reaction temperature may be from 0° to 100° C., and the reaction is completed instantaneously or within 10 hours.

(c) A process comprising reaction of an aniline derivative of the formula:

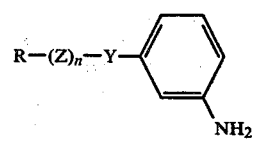

(IV)

wherein, R, Y, Z and n are each as defined above, with methyl isocyanate, N-methoxy-N-methylcarbamyl chloride or N,N-dimethylcarbamyl chloride.

This reaction is carried out by treatment of the aniline derivative (IV) with methyl isocyanate, N-methoxy-N-methylcarbamyl chloride or N,N-dimethylcarbamyl chloride in a molar proportion of 1:1–5 in an organic solvent (e.g. benzene, toluene, xylene, diethyl ether, tetrahydrofuran, dioxane, chloroform, carbon tetrachloride, ethyl acetate, pyridine, dimethylformamide), preferably in the presence of a hydrogen chloride-eliminating agent (e.g. pyridine, triethylamine, sodium hydroxide, potassium hydroxide) in an amount of 1–5 mol per 1 mol of the aniline derivative (IV). The reaction is usually effected at a temperature of 0° to 150° C. instantaneously or within 10 hours.

(d) A process comprising reaction of a reactive compound of the formula:

R—(Z)$_n$—X  (V)

wherein X is a halogen atom, a mesyloxy group or a tosyloxy group and R, Z and n are each as defined above, with an N'-phenyl-N-methylurea derivative of the formula:

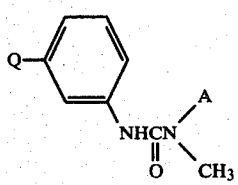

wherein Q is a hydroxyl group or a mercapto group and A is as defined above.

This reaction is carried out by treating the reactive compound (V) with the N'-phenyl-N-methylurea (VI) in a molar proportion of 1:1–15. in an organic solvent (e.g. benzene, toluene, xylene, diethyl ether, tetrahydrofuran, dioxane, chloroform, carbon tetrachloride, methylene chloride, ethyl acetate, methanol, ethanol, isopropanol, N,N-dimethylformamide), water or a mixture thereof in the presence of a base (e.g. pyridine, triethylamine, sodium hydroxide, potassium hydroxide, sodium carbonate, sodium ethoxide) in an amount of 1–1.5 mol per 1 mol of the reactive compound (V). The existence of a phase transfer catalyst such as a quaternary ammonium salt in an amount of 0.1–10 mol % based on the reactive compound (V) is advantageous in the reaction.

The phenylisocyanate derivative (II) in the process (a) can easily be obtained by the reaction between the aniline derivative (IV) and phosgene, usually in a molar proportion of 1:1–5. This reaction is carried out in an organic solvent (e.g. benzene, toluene, xylene, tetrahydrofuran, dioxane, chloroform, carbon tetrachloride, ethyl acetate), usually at a temperature from room temperature (e.g. 20° C.) to the refluxing temperature of the solvent instantaneously or within 10 hours.

The N'-phenyl-N-hydroxyurea derivative (III) in the process (b) can be obtained by the reaction between the phenylisocyanate derivative (II) and hydroxylamine in an molar proportion of 1:1–5. This reaction is carried out in an organic solvent (e.g. benzene, toluene, xylene, diethyl ether, tetrahydrofuran, dioxane, chloroform, carbon tetrachloride), water or a mixture thereof usually at a temperature of 0° to 50° C. instantaneously or within 10 hours.

The aniline derivative (III), which is the starting material in the processes (a), (b), (c) and (d), is obtainable by reduction of the corresponding nitrobenzene of the formula:

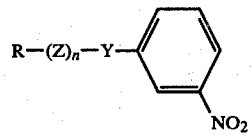

wherein R, Y, Z and n are each as defined above. The reduction may be accomplished by any conventional procedure such as catalytic reduction using platinum oxide, Raney nickel, platinum black, palladium black or the like, reduction with a metal (e.g. tin, iron, zinc) and an acid (e.g. hydrochloric acid, sulfuric acid), reduction with a metal (e.g. sodium, lithium, aluminum, magnesium, zinc) in an alcohol, reduction with a metal (e.g. sodium, zinc) and an aqueous or alcoholic alkali, reduction with an inorganic compound (e.g. stannous chloride, ferrous sulfate, ferrous hydroxide, sodium sulfide, sodium polysulfide, ammonium sulfide, hydrogen sulfide) or reduction with a hydrazine compound (e.g. hydrazine, phenylhydrazine). For instance, in case of catalytic reduction using platinum oxide, the reduction may be effected by treatment with hydrogen in an inert solvent (e.g. benzene, toluene, ethanol, methanol, isopropanol, tetrahydrofuran, dioxane) under atmospheric or elevated pressure for a period of 30 minutes to 10 hours.

The nitrobenzene drivative (VII) is obtainable by the condensation-reaction between a reactive compound of the formula:

$$R-(Z)_n-X \qquad (VIII)$$

wherein X is a halogen atom, a mesyloxy group or a tosyloxy group and R, Z and n are each as defined above, and the alkali metal salt of m-nitrophenol or m-nitrothiophenol in a molar proportion of 1:1–1.5. The reaction is usually carried out in an organic solvent (e.g. benzene, toluene, xylene, diemthylformamide, ethanol, methanol) or water, or a mixture thereof. The reaction is effected, if necessary, under cooling or under heating (e.g. 20° C. to the refluxing temperature of the solvent) instantaneously or within 10 hours. The existence of a phase transfer catalyst such as a quaternary ammonium salt is favorable for obtaining the objective compound in a high yield.

The reactive compound (VIII), which is the starting material in the synthesis of the nitrogenzene derivative (VII), is producible from the corresponding known alcohol of the formula:

$$R-(Z)_n-OH$$

wherein R, Z and n are each as defined above by a per se conventional procedure [S. R. Sandler and W. Karo: "Organic Functional Group Preparations", Academic Press, New York (1968), Chapter 6 and 21].

Some examples of the compounds (I) are shown below.

| Compound No. | Chemical structure | Melting point or refractive index |
|---|---|---|
| 1 | [structure] | M.P., 56–57° C. |

-continued

| Compound No. | Chemical structure | Melting point or refractive index |
|---|---|---|
| 2 | cyclopropyl-CH₂CH₂O-C₆H₄-NHC(=O)N(CH₃)(CH₃) | M.P., 118–119° C. |
| 3 | cyclohexyl-O-C₆H₄-NHC(=O)N(OCH₃)(CH₃) | M.P., 94–96° C. |
| 4 | cyclohexyl-O-C₆H₄-NHC(=O)N(CH₃)(CH₃) | M.P., 150–151° C. |
| 5 | cyclohexyl-CH₂O-C₆H₄-NHC(=O)N(OCH₃)(CH₃) | M.P., 75–76° C. |
| 6 | cyclohexyl-CH₂O-C₆H₄-NHC(=O)N(CH₃)(CH₃) | M.P., 77–78° C. |
| 7 | cyclohexyl-CH₂CH₂O-C₆H₄-NHC(=O)N(OCH₃)(CH₃) | M.P., 81–82° C. |
| 8 | cyclohexyl-CH₂CH₂O-C₆H₄-NHC(=O)N(CH₃)(CH₃) | M.P., 128–129° C. |
| 9 | CH₃-cyclohexyl-CH₂CH₂O-C₆H₄-NHC(=O)N(OCH₃)(CH₃) | M.P., 53–55° C. |
| 10 | CH₃-cyclohexyl-CH₂CH₂O-C₆H₄-NHC(=O)N(CH₃)(CH₃) | M.P., 117–118° C. |
| 11 | cyclohexyl-CH₂S-C₆H₄-NHC(=O)N(OCH₃)(CH₃) | $n_D^{25}$ 1.5629 |

-continued

| Compound No. | Chemical structure | Melting point or refractive index |
|---|---|---|
| 12 | Cyclohexyl-CH₂S-C₆H₄-NHC(=O)N(CH₃)₂ | M.P., 111–112° C. |
| 13 | Cyclohexyl-OCH₂CH₂O-C₆H₄-NHC(=O)N(OCH₃)(CH₃) | M.P., 85–86° C. |
| 14 | Cyclohexyl-OCH₂CH₂O-C₆H₄-NHC(=O)N(CH₃)₂ | M.P., 142–143° C. |
| 15 | Cyclohexyl-OCH₂CH₂O-C₆H₄-NHC(=O)N(CH₃)(H) | M.P., 105–106° C. |
| 16 | Cyclohexenyl-CH₂CH₂O-C₆H₄-NHC(=O)N(CH₃)(H) | M.P., 96–97° C. |
| 17 | Cycloheptyl-O-C₆H₄-NHC(=O)N(OCH₃)(CH₃) | M.P., 60–61° C. |
| 18 | Cycloheptyl-O-C₆H₄-NHC(=O)N(CH₃)₂ | M.P., 103–104° C. |
| 19 | Adamantyl-CH₂CH₂O-C₆H₄-NHC(=O)N(OCH₃)(CH₃) | M.P., 83–86° C. |
| 20 | Adamantyl-CH₂CH₂O-C₆H₄-NHC(=O)N(CH₃)₂ | M.P., 152–154° C. |

-continued

| Compound No. | Chemical structure | Melting point or refractive index |
|---|---|---|
| 21 | indan-2-yl-O-C6H4-NHC(O)N(OCH3)(CH3) | M.P., 117–119° C. |
| 22 | indan-2-yl-O-C6H4-NHC(O)N(CH3)(CH3) | M.P., 150–151° C. |
| 23 | cyclopentyl-CH2CH2CH2O-C6H4-NHC(O)N(OCH3)(CH3) | M.P., 70–71° C. |
| 24 | cyclopentyl-CH2CH2CH2O-C6H4-NHC(O)N(CH3)(CH3) | M.P., 118–119° C. |
| 25 | cyclopentyl-CH2CH2CH2O-C6H4-NHC(O)N(CH3)(H) | M.P., 94–96° C. |
| 26 | cyclohexyl-CH2CH2S-C6H4-NHC(O)N(OCH3)(CH3) | $n_D^{23.5}$ 1.5662 |
| 27 | cyclohexyl-CH2CH2S-C6H4-NHC(O)N(CH3)(CH3) | M.P., 101–102° C. |
| 28 | (bicyclic)-CH2O-C6H4-NHC(O)N(OCH3)(CH3) | M.P., 97–98° C. |
| 29 | (bicyclic)-CH2O-C6H4-NHC(O)N(CH3)(CH3) | M.P., 113–114° C. |
| 30 | tetrahydronaphth-2-yl-O-C6H4-NHC(O)N(OCH3)(CH3) | $n_D^{24}$ 1.5530 |

-continued

| Compound No. | Chemical structure | Melting point or refractive index |
|---|---|---|
| 31 | (norbornyl)-CH₂O-(C₆H₄)-NHC(=O)N(OCH₃)(CH₃) | M.P., 74–75° C. |
| 32 | (norbornyl)-CH₂O-(C₆H₄)-NHC(=O)N(CH₃)(CH₃) | M.P., 116–117° C. |
| 33 | (norbornyl)-CH₂CH₂O-(C₆H₄)-NHC(=O)N(OCH₃)(CH₃) | M.P., 93–94° C. |
| 34 | (norbornyl)-CH₂CH₂O-(C₆H₄)-NHC(=O)N(CH₃)(CH₃) | M.P., 153–154° C. |
| 35 | (2-methylcyclohexyl)-CH₂CH₂O-(C₆H₄)-NHC(=O)N(OCH₃)(CH₃) | $n_D^{22}$ 1.5389 |
| 36 | (2-methylcyclohexyl)-CH₂CH₂O-(C₆H₄)-NHC(=O)N(CH₃)(CH₃) | M.P., 84–86° C. |
| 37 | (3-methylcyclohexyl)-CH₂CH₂O-(C₆H₄)-NHC(=O)N(OCH₃)(CH₃) | M.P., 50–52° C. |
| 38 | (3-methylcyclohexyl)-CH₂CH₂O-(C₆H₄)-NHC(=O)N(CH₃)(CH₃) | M.P., 117–118° C. |

-continued

| Compound No. | Chemical structure | Melting point or refractive index |
|---|---|---|
| 39 | 3-methylcyclohexyl-CH₂CH₂CH₂O-C₆H₄-NHC(=O)N(OCH₃)(CH₃) | M.P., 61–62° C. |
| 40 | 3-methylcyclohexyl-CH₂CH₂CH₂O-C₆H₄-NHC(=O)N(CH₃)₂ | M.P., 125–126° C. |
| 41 | (1,2,3,4-tetrahydronaphthalen-1-yl)-CH₂CH₂O-C₆H₄-NHC(=O)N(OCH₃)(CH₃) | M.P., 69–70° C. |
| 42 | (1,2,3,4-tetrahydronaphthalen-1-yl)-CH₂CH₂O-C₆H₄-NHC(=O)N(CH₃)₂ | M.P., 123–124° C. |
| 43 | (indan-2-yl)-CH₂CH₂O-C₆H₄-NHC(=O)N(OCH₃)(CH₃) | M.P., 75–76° C. |
| 44 | (indan-2-yl)-CH₂CH₂O-C₆H₄-NHC(=O)N(CH₃)₂ | M.P., 130–131° C. |
| 45 | cyclohex-1-enyl-CH₂CH₂O-C₆H₄-NHC(=O)N(OCH₃)(CH₃) | M.P., 81–82° C. |
| 46 | cyclohex-1-enyl-CH₂CH₂O-C₆H₄-NHC(=O)N(CH₃)₂ | M.P., 106–107° C. |
| 47 | norbornan-2-yl-CH₂CH₂CH₂O-C₆H₄-NHC(=O)N(OCH₃)(CH₃) | M.P., 74–76° C. |

-continued

| Compound No. | Chemical structure | Melting point or refractive index |
|---|---|---|
| 48 | norbornyl-CH₂CH₂CH₂O-C₆H₄-NHC(O)N(CH₃)(CH₃) | M.P., 138–139° C. |
| 49 | cyclobutyl-CH₂O-C₆H₄-NHC(O)N(OCH₃)(CH₃) | M.P., 93–94° C. |
| 50 | cyclobutyl-CH₂O-C₆H₄-NHC(O)N(CH₃)(CH₃) | M.P., 154–155° C. |
| 51 | indanyl-CH₂CH₂O-C₆H₄-NHC(O)N(OCH₃)(CH₃) | M.P., 81–82° C. |
| 52 | indanyl-CH₂CH₂O-C₆H₄-NHC(O)N(CH₃)(CH₃) | M.P., 102–103° C. |
| 53 | norbornyl-CH₂CH₂O-C₆H₄-NHC(O)N(CH₃)(H) | M.P., 120–121° C. |
| 54 | (2-methylcyclohexyl)-CH₂CH₂O-C₆H₄-NHC(O)N(CH₃)(H) | M.P., 55–58° C. |
| 55 | (3-methylcyclohexyl)-CH₂CH₂O-C₆H₄-NHC(O)N(CH₃)(H) | $n_D^{23}$ 1.5424 |
| 56 | indanyl-CH₂CH₂O-C₆H₄-NHC(O)N(CH₃)(H) | M.P., 135–136° C. |

-continued

| Compound No. | Chemical structure | Melting point or refractive index |
|---|---|---|
| 57 | [norbornyl]–CH$_2$CH$_2$O–[phenyl]–NHC(=O)N(CH$_3$)(H) | n$_D^{25.5}$ 1.5568 |
| 58 | [cyclobutyl]–CH$_2$O–[phenyl]–NHC(=O)N(CH$_3$)(H) | M.P., 148–149° C. |
| 59 | 2,4-dimethylcyclohexyl–CH$_2$CH$_2$O–[phenyl]–NHC(=O)N(CH$_3$)(H) | n$_D^{25}$ 1.5425 |
| 60 | 2,4-dimethylcyclohexyl–CH$_2$CH$_2$O–[phenyl]–NHC(=O)N(OCH$_3$)(CH$_3$) | M.P., 75–76° C. |
| 61 | 2,4-dimethylcyclohexyl–CH$_2$CH$_2$O–[phenyl]–NHC(=O)N(CH$_3$)(CH$_3$) | M.P., 88–89° C. |
| 62 | 2,4-dimethylcyclohexyl–CH$_2$CH$_2$O–[phenyl]–NHC(=O)N(CH$_3$)(H) | n$_D^{25}$ 1.5471 |
| 63 | 2,4-dimethylcyclohexyl–CH$_2$CH$_2$O–[phenyl]–NHC(=O)N(CH$_3$)(CH$_3$) | M.P., 66–67.5° C. |
| 64 | 2,4-dimethylcyclohexyl–CH$_2$CH$_2$O–[phenyl]–NHC(=O)N(OCH$_3$)(CH$_3$) | n$_D^{25.5}$ 1.5318 |

Practical and presently preferred embodiments of the preparation of the compounds (I) are illustratively shown in the following examples.

EXAMPLE 1 (PROCEDURE (A))

To a solution of 5.6 g of 3-(2-cyclohexyltoluene)-phenyl isocyanate in 100 ml of benzene was added dropwise a solution of 3 g of N,O-dimethylhydroxylamine in 50 ml of benzene at a temperature below 30° C. The reaction mixture was stirred at room temperature for 30 minutes, and the solvent was then removed under reduced pressure. The residue was recrystallized from ethanol to give 5.5 g of N'-3-[2-(2-cyclohexyl)ethoxy]- phenyl-N-methoxy-N-methylurea as white crystals. M.P., 81°-82° C.

Elementary analysis: Calcd. for $C_{17}H_{26}O_3N_2$: C, 66.64%; H, 8.55%; N, 9.14%. Found: C, 66.74%; H, 8.69%; N, 8.85%.

NMR$\delta_{CDCl_3}$: 0.6-2.0 (13H), 3.09 (s, 3H), 3.65 (s, 3H), 3.88 (t, 2H), 6.3-7.2 (4H), 7.5 (s, 1H).

EXAMPLE 2 (PROCEDURE (A))

To a solution of 9 g of 3-[2-(1-adamantane)ethoxy]phenyl isocyanate in 100 ml of benzene was added dropwise a solution of 3.5 g of N,O-dimethylhydroxylamine in 50 ml of benzene at a temperature below 30° C. The reaction mixture was stirred at room temperature for 30 minutes, and the solvent was then removed under reduced pressure. The residue was recrystallized from ethanol to give 8.5 g of N'-3-[2-(1-adamantane)ethoxy]phenyl-N-methoxy-N-methylurea as white crystals. M.P., 83°-86° C.

Elementary analysis: Calcd. for $C_{21}H_{30}O_3N_2$: C, 70.36%; H, 8.44%; N, 7.82%. Found: C, 70.31%; H, 8.68%; N, 7.62%.

NMR$\delta_{CDCl_3}$: 1.3-2.4 (17H), 3.10 (s, 3H), 3.65 (s, 3H), 3.91 (t, 2H), 6.3-7.2 (4H), 7.45 (s, 1H).

In the same manner as above, the compounds (I) such as Compound Nos. 1, 5, 8, 11, 12, 17, 21, 23, 24, 28, 29, 30, 33, 34, 35, 36, 39, 41, 42, 43, 44, 51 and 52 were synthesized.

EXAMPLE 3 (PROCEDURE (B))

To a solution of 5.88 g of N'-3-[2-(cyclohexyloxy)ethoxy]phenyl-N-hydroxyurea and 5.54 g of dimethyl sulfate in 60 ml of toluene was added 0.065 g of tetra-n-butyl-ammonium bromide. To the solution, 4.4 ml of 10 N aqueous sodium hydroxide solution was added dropwise at 20° to 22° C. The resultant mixture was diluted with water and extracted with toluene. The toluene extract was dried over anhydrous sodium sulfate and concentrated. The residue was purified by column chromatography on silica gel with an eluent of benzene and tetrahydrofuran (3:1) to give 5.5 g of N-3-[2-(cyclohexyloxy)ethoxy]phenyl-N-methoxy-N-methylurea. M.P., 85°-86° C.

Elementary analysis: Calcd. for $C_{17}H_{26}O_4N_2$: C, 63.33%; H, 8.13%; N, 8.69%. Found: C, 63.41%; H, 8.28%; N, 8.80%.

NMR$\delta_{CDCl_3}$: 1.0-2.1 (10H), 3.05 (s, 3H), 3.15 (m, 1H), 3.61 (s, 3H), 3.62 (t, 2H), 3.95 (t, 2H), 6.2-7.1 (4H), 7.40 (s, 1H).

In the same manner as above, the compounds (I) such as Compound Nos. 26 and 47 were synthesized.

EXAMPLE 4 (PROCEDURE (C))

To a solution of 3.5 g of 3-[2-(4-methylcyclohexyl)ethoxy]aniline and 4 ml of triethylamine in 100 ml of dimethylformamide was added 3 g of N,N-dimethylcarbamoyl chloride. The mixture was heated at 50° to 55° C. for 3 hours and thereafter allowed to stand overnight. The reaction mixture was diluted with water and extracted with benzene. The benzene extract was dried over anhydrous sodium sulfate and concentrated. The resulting product was purified by column chromatography on silica gel with an eluent of benzene and tetrahydrofuran (3:1) to give 2.5 g of N'-3-[2-(4-methylcyclohexyl)ethoxy]phenyl-N,N-dimethylurea. M.P., 117°-118° C.

Elementary analysis: Calcd. for $C_{18}H_{28}O_2N_2$: C, 71.01%; H, 9.27%; N, 9.20%. Found: C, 70.82%; H, 9.57%; N, 9.13%.

NMR$\delta_{CDCl_3}$: 0.9 (d, 3H), 1.0-1.9 (12H), 2.89 (s, 6H), 3.81 (t, 2H), 6.0-7.1 (5H).

In the same manner as above, the compounds (I) such as Compound Nos. 2, 4, 6, 9, 15, 16, 20, 22, 25, 27, 31, 32, 37, 38, 45, 46, 50, 53, 54, 55, 56, 57 and 58 were synthesized.

EXAMPLE 5 (PROCEDURE (D))

To a solution of 6.8 g of sodium ethoxide and 18 g of N-3-hydroxyphenyl-N,N-dimethylurea in 200 ml of dimethylformamide was added dropwise 17.7 g of cycloheptyl bromide. The resultant mixture was heated at 90° C. for 1 hour, diluted with water and extracted with benzene. The solvent was removed under reduced pressure. The resulting product was purified by column chromatography on silica gel with an eluent of benzene and tetrahydrofuran (3:1) to give 11.6 g of N'-3-(cycloheptyloxy)phenyl-N,N-dimethylurea. M.P., 103°-104° C.

Elementary analysis: Calcd. for $C_{16}H_{24}O_2N_2$: C, 69.53%; H, 8.75%; N, 10.14%. Found: C, 69.54%; H, 8.69%; N, 10.18%.

NMR$\delta_{CDCl_3}$: 1.2-2.1 (12H), 2.90 (s, 6H), 4.30 (m, 1H), 6.2-7.1 (5H).

In the same manner as above, the compounds (I) such as Compound Nos. 14, 40, 48 and 49 were synthesized.

EXAMPLE 6 (SYNTHESIS OF THE PHENYL ISOCYANATE DERIVATIVE (II))

A solution of 14.5 g of 3-[2-(cyclohexyloxy)-ethoxy]aniline in 100 ml of toluene was added dropwise to 100 ml of toluene containing 12 g of phosgene. The resultant mixture was refluxed for 1 hour and concentrated under reduced pressure. The concentrate was purified by high vacuum distillation to give 14 g of 3-[2-(cyclohexyloxy)-ethoxy]phenyl isocyanate. B.P., 112°-115° C./0.06 mmHg. $n_D^{23}$ 1.5283.

Elementary analysis: Calcd. for $C_{15}H_{19}NO_3$: C, 68.94%; H, 7.33%; N, 5.36%. Found: C, 68.98%; H, 7.21%; N, 5.47%.

NMR$\delta_{CCl_4}$: 1.0-2.1 (10H), 3.25 (m, 1H), 3.60 (t, 2H), 3.91 (t, 2H), 6.2-7.2 (4H).

In the same manner as in Example 6, the following phenyl isocyanate derivatives were produced:

| Chemical structure | Physical property |
|---|---|
| ⟨H⟩—CH₂CH₂S—⟨◯⟩\NCO | B.P., 115-116° C./ 0.1 mmHg; $n_D^{24}$ 1.5674 |

EXAMPLE 7 (SYNTHESIS OF THE ANILINE DERIVATIVE (IV))

A suspension of 14 g of 3-[2-(1-adamantane)ethoxy]nitrobenzene and 1 g of 10% palladium-carbon in 100 ml of benzene-ethanol solution (1:1) was subjected to catalytic reduction under room temperature and atmospheric pressure, whereby 2.7 liters of hydrogen were absorbed. The resulting mixture was filtered and concentrated under reduced pressure. The precipitated crystals were collected by filtration and washed with ether to give 11.3 g of 3-[3-(1-adamantane)-ethoxy]aniline. M.P., 60°–61° C.

Elementary analysis: Calcd. for $C_{18}H_{25}ON$: C, 79.66%; H, 9.29%; N, 5.16%. Found: C, 79.76%; H, 9.13%; N, 5.03%.

NMR$\delta_{CDCl_3}$: 1.4–2.1 (17H), 3.5 (s, 2H), 3.85 (t, 2H), 5.9–7.0 (4H).

In the same manner as in Example 7, the following aniline derivatives were produced:

| Chemical structure | Physical property |
|---|---|
| [H]>—CH₂CH₂O—[Ar]NH₂ (cyclopentyl) | M.P., 29–30° C. |
| [H]—CH₂CH₂O—[Ar]NH₂ (cyclohexyl) | B.P., 120—120° C./ 0.2 mmHg |
| H₃C—[H]—CH₂CH₂O—[Ar]NH₂ | B.P., 135–145° C./ 0.09 mmHg |
| [H]—CH₂S—[Ar]NH₂ | B.P., 133–138° C./ 0.08 mmHg |
| [H]—OCH₂CH₂O—[Ar]NH₂ | B.P., 137–150° C./ 0.4 mmHg |
| [phenyl]—CH₂CH₂O—[Ar]NH₂ | B.P., 138–145° C./ 0.09 mmHg |
| [H]—O—[Ar]NH₂ | B.P., 146–150° C./ 0.15 mmHg |
| [H]>—CH₂CH₂CH₂O—[Ar]NH₂ | M.P., 28–29° C. |
| [H]—CH₂CH₂S—[Ar]NH₂ | B.P., 145–148° C./ 0.15 mmHg |
| [indanyl]—CH₂CH₂O—[Ar]NH₂ | M.P., 49–50° C. |
| [norbornyl]—CH₂CH₂O—[Ar]NH₂ | B.P., 143–148° C./ 0.09 mmHg |
| H₃C—[H(CH₃)]—CH₂CH₂O—[Ar]NH₂ (with CH₃ groups) | B.P., 152–155° C./ 0.3 mmHg |

EXAMPLE 8 (SYNTHESIS OF THE HYDROXYUREA DERIVATIVE (III))

To a solution of 4 g of hydroxylamine hydrochloride in 10 ml of water, 8 ml of 10 N aqueous sodium hydroxide solution were added dropwise under ice-cooling. To the mixture a solution of 10 g of 3-[2-(cyclohexyloxy)ethyl]-phenyl isocyanate in 100 ml of toluene was added dropwise at 10° C. After allowed to stand overnight, the resultant mixture was diluted with water and extracted with benzene. The benzene extract was dried over anhydrous magnesium sulfate and concentrated to obtain 7 g of crude crystals of N'-3-[2-(cyclohexyloxy)ethoxy]-phenyl-N-hydroxyurea. Recrystallization from ethanol gave needles melting at 171° to 173° C.

Elementary analysis: Calcd. for $C_{15}H_{22}O_4N_2$: C, 61.20%; H, 7.53%; N, 9.52%. Found: C, 61.18%; H, 7.55%; N, 9.56%.

NMR$\delta_{CDCl_3\text{-}DMSO\text{-}d_6}$: 1.0–2.1 (10H), 3.0–3.5 (2H), 3.70 (m, 2H), 3.95 (m, 2H), 6.3–7.3 (4H), 8.80 (1H), 9.51 (s, 1H).

In the same manner as in Example 8, the following hydroxyurea derivative was produced:

| Chemical structure | Physical property |
|---|---|
| [H]—CH₂CH₂S—[Ar]—NHCN(=O)(OH)(H) | M.P., 112–114° C. |

EXAMPLE 9 (SYNTHESIS OF THE NITROBENZENE DERIVATIVE (VII))

To a solution of 6.8 g of sodium ethoxide and 15 g of m-nitrophenol in 250 ml of dimethylformamide, 28 g of cyclohexyloxyethyl p-toluenesulfonate were added. After heating at 100° C. for 2 hours, the resulting mixture was diluted with water and extracted with benzene. The solvent was removed under reduced pressure, and the residue was purified by vacuum distillation to give 23.8 g of 3-[2-(cyclohexyloxy)ethoxy]nitrobenzene. B.P., 118°–124° C./0.1 mmHg. $n_D^{27}$ 1.5380.

Elementary analysis: Calcd. For $C_{14}H_{19}O_4N$: C, 63.38%; H, 7.22%; N, 5.28%. Found: C, 63.31%; H, 7.21%; N, 5.19%.

NMR$\delta_{CCl_4}$: 1.0–2.1 (10H), 3.3 (m, 1H), 3.71 (m, 2H), 4.15 (m, 2H), 7.0–7.9 (4H).

In the same manner as in Example 9, the following nitrobenzene derivatives were produced:

| Chemical structure | Physical property |
|---|---|
| (indane)-O-(phenyl-NO₂) | M.P., 85–86° C. |
| (indane)-CH₂CH₂O-(phenyl-NO₂) | M.P., 76–77° C. |
| (adamantane)-CH₂CH₂O-(phenyl-NO₂) | M.P., 55–58° C. |

In the practical usage of the compounds (I), they may be applied as such or in any preparation forms such as wettable powders, emulsifiable concentrates, suspensions, granules, fine granules or dusts.

In producing such preparation form, a solid or liquid carrier may be used. As for the solid carrier, there may be given mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like.

As for the liquid carrier, there may be given alcohols (e.g. methyl alcohol, ethyl alcohol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methyl ethyl ketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene polymers, oxypropylene polymers, polyoxyethylene alkyl phosphates, fatty acid salts, alkyl sulfates, alkyl sulfonates, alkylaryl sulfonates, alkyl phosphates, quaternary ammonium salts and the like. But, the surface active agent is not of course limited to these compounds. And, if necessary, gelatin, casein, sodium alginate, starch, agar, polyvinyl alcohol or the like may be used as an auxiliary agent.

In the preparation of a herbicidal composition, the content of the compound (I) may be from 1 to 95% by weight, preferably from 5 to 80% by weight.

Practical embodiments of the herbicidal composition according to the invention are illustratively shown in the following examples wherein parts and % are by weight.

PREPARATION EXAMPLE 1

Eighty parts of Compound No. 19, 5 parts of polyoxyethylene alkylaryl ether and 15 parts of synthetic silicon oxide hydrate are well mixed while being powdered to obtain a wettable powder.

PREPARATION EXAMPLE 2

Thirty parts of Compound No. 28, 7 parts of polyoxyethylene alkylaryl ether, 3 parts of alkylaryl sulfonate and 60 parts of xylene are well mixed to obtain an emulsifiable concentrate.

PREPARATION EXAMPLE 3

Five parts of Compound No. 7, 1 part of white carbon, 5 parts of ligninsulfonate and 89 parts of clay are well mixed while being powdered. The mixture is then well kneaded with water, granulated and dried to obtain granules.

PREPARATION EXAMPLE 4

Fourty parts of bentonite, 5 parts of ligninsulfonate and 55 parts of clay are well mixed while being powdered. The mixture is then well kneaded with water, granulated and dried to obtain granules containing no active ingredient. The granules are then impregnated with 5 parts of Compound No. 21.

PREPARATION EXAMPLE 5

Five parts of Compound No. 24, 0.5 part of isopropyl phosphate, 64.5 parts of clay and 30 parts of talc are well mixed while being powdered to obtain a dust.

PREPARATION EXAMPLE 6

Twenty parts of Compound No. 38 are mixed with 60 parts of a 3% aqueous solution of polyoxyethylene sorbitan monolaurate and pulverized in a wetting condition until the active ingredient becomes a particle size of 3 microns or less. Twenty parts of a 3% aqueous solution of sodium alginate as a dispersing stabilizer are added thereto to obtain 100 parts of a dispersion.

The compounds (I) of the invention may be used together with other herbicides and/or fungicides to improve their activity as herbicides, and in some cases, a synergistic effect can be expected. As the other herbicides or fungicides, there may be given 2,4-dichlorophenoxyacetic acid, sodium 5-[2-chloro-4-(trifluoromethyl)phenoxy]-2-nitrobenzoate, 2-chloro-4-ethylamino-6-isopropyl, amino S-triazine, 2-methylthio-4,6-bis(isopropylamino)-S-triazine, 3-(3,4-dichlorophenyl)-1,1-dimethylurea, 3-[4-(4-chlorophenoxy)phenyl]-1,1-dimethylurea, 3-(α,α,α-trifluoro-m-tolyl)-1,1-dimethylurea, isopropyl-N-(3-chlorophenyl)-carbamate, 3,4-dichloropropyonanilide, 3-cyclohexyl-5,6-trimethyluracil, O-methyl-O-(2-nitro-5-methylphenyl)-N-secbutylphosphoroamidothioate, 3-isopropyl-1H-2,1,3-benzothiadiazine(4)-3H-one-2,2-dioxide, disodium methanearsonate, N-(3,5-dichlorophenyl)-1,2-dimethylcyclopropane-1,2-dicarboximide, S-n-butyl-S-p-tert-butylbenzyl-N-3-pyridylcarbonimidate, O,O-dimethyl-O-2,6-dichloro-4-methylphenylphosphorothioate, methyl-N-benzimidazol-2-yl-N-(butylcarbamoyl)carbamate, N-trichloromethylthio-4-cyclohexene-1,2-dicarboximide, cis-N-(1,1,2,2-tetrachloroethylthio)-4-cyclohexene-1,2-dicarboximide, polyoxin, streptomycin, zinc ethylenebisdithiocarbamate, zinc dimethylthiocarbamate, manganese ethylenebisdithiocarbamate, bis(dimethylthiocarbamoyl)disulfide, tetrachloroisophthanonitrile, 8-hydroxyquinone, dodecylguanidine acetate, 5,6-dihydro-2-methyl-1,4-oxathiin-3-carboxanilide, N'-dichlorofluoromethylthio-N,N-dimethyl-N'-phenylsulfamide, 1-(4-chlorophenoxy)-3,3-dimethyl-1-(1,2,4-triazol-1-yl)-2-butane, 1,2-bis(3-methoxycarbonyl-2-thioureido)benzene and the like. But, the herbicides and/or fungicides are not of course limited to these examples.

The herbicides of the invention may be applied together with microbicidal agricultural chemicals, organic phosphorus series insecticides, carbamate series insecticides, pyrethroid series insecticides, other insecticides, plant growth regulators, fertilizers, etc.

The dosage rate of the compounds (I) depends upon their kinds, the sorts of cultivated plants, the method of application, wheather, etc. Generally, however, the dosage rate is from 1 to 200 grams, preferably from 5 to 50 grams, of the active ingredient per are.

The application of the compounds (I) as herbicides will be illustrated in the following Examples wherein the phytotoxicity to cultivated plants and the herbicidal activity on weeds were evaluated as follows: the aereal parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and to control weeds, respectively. The rating values in the paddy rice test alone were calculated from the dry weight of plant.

| Rating value | Fresh weight (percentage to untreated plot) | |
|---|---|---|
| | Cultivated plant | Weed |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following control compounds were used in the Examples.

Chloroxuron

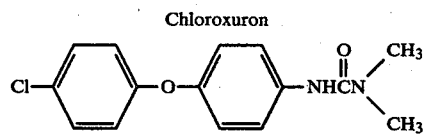

Fluometuron

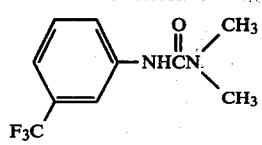

Chloramben

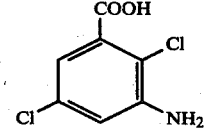

MCP

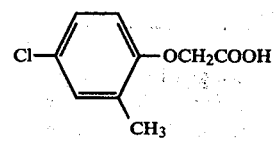

Control (a)

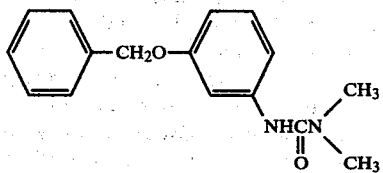

Example A (Post-emergence application test)

Plastic trays (35 cm×25 cm×10 cm (high)) were filled with upland field soil, and the seeds of redroot pigweed, common lambsquarters, radish, sunflower, cocklebur, tall morningglory, black nightshade, large crabgrass, barnyardgrass and green foxtail were separately sowed in the trays and grown for 3 weeks in a greenhouse. The required amount of the test compound was sprayed to the foliage of the test plants over the top by means of a small hand sprayer. After the spraying, the test plants were grown for further 3 weeks in the greenhouse, and the herbicidal activity was examined. The results are shown in Table 1. In the above foliar application, the test compounds were each formulated into an emulsifiable concentrate, and the required amount of the emulsifiable concentrate was dispersed in water for application at a spray volume of 5 liters per are and applied with the addition of a wetting agent. At the time of application, the weeds were in a 2 to 4 leaf stage and 2 to 10 cm in height although there was some difference depending upon the kind of weed.

TABLE 1

| Compound No. | Dosage (weight of active ingredient, g/are) | Herbicidal activity | | | | | | | | | |
|---|---|---|---|---|---|---|---|---|---|---|---|
| | | Redroot pigweed | Common lambsquarters | Radish | Sunflower | Cocklebur | Tall morningglory | Black nightshade | Large crabgrass | Barnyardgrass | Green foxtail |
| 1 | 20 | 5 | 5 | 5 | 5 | 5 | 5 | 5 | 5 | 5 | 5 |
|  | 10 | 5 | 5 | 5 | 5 | 5 | 5 | 5 | 4 | 4 | 5 |
| 3 | 20 | 5 | 5 | 5 | 5 | 5 | 5 | 5 | 4 | 5 | 5 |
|  | 10 | 5 | 5 | 5 | 5 | 5 | 5 | 5 | 4 | 4 | 4 |
| 4 | 20 | 5 | 5 | 5 | 5 | 5 | 5 | 5 | 4 | 4 | 4 |
|  | 10 | 5 | 5 | 5 | 5 | 5 | 5 | 5 | 3 | 4 | 4 |
| 5 | 20 | 5 | 5 | 5 | 5 | 5 | 5 | 5 | 5 | 4 | 5 |
|  | 10 | 5 | 5 | 5 | 5 | 5 | 5 | 5 | 4 | 4 | 4 |
| 6 | 20 | 5 | 5 | 5 | 5 | 5 | 5 | 5 | 4 | 4 | 4 |

TABLE 1-continued

| Compound No. | Dosage (weight of active ingredient, g/are) | Herbicidal activity | | | | | | | | | |
|---|---|---|---|---|---|---|---|---|---|---|---|
| | | Redroot pigweed | Common lambsquarters | Radish | Sunflower | Cocklebur | Tall morningglory | Black nightshade | Large crabgrass | Barnyardgrass | Green foxtail |
| 7 | 10 | 5 | 5 | 5 | 4 | 5 | 4 | 5 | 4 | 3 | 4 |
| | 20 | 5 | 5 | 5 | 5 | 5 | 5 | 5 | 5 | 5 | 5 |
| 8 | 10 | 5 | 5 | 5 | 5 | 5 | 5 | 5 | 4 | 4 | 5 |
| | 20 | 5 | 5 | 5 | 5 | 5 | 5 | 5 | 4 | 4 | 5 |
| 9 | 10 | 5 | 5 | 5 | 5 | 5 | 5 | 5 | 4 | 4 | 4 |
| | 20 | 5 | 5 | 5 | 5 | 5 | 5 | 5 | 4 | 4 | 5 |
| 11 | 10 | 5 | 5 | 5 | 5 | 5 | 5 | 5 | 3 | 4 | 3 |
| | 40 | 5 | 5 | 5 | 5 | 5 | 5 | 5 | 4 | 5 | 4 |
| 13 | 20 | 5 | 5 | 5 | 5 | 5 | 5 | 5 | 4 | 3 | 4 |
| | 10 | 5 | 5 | 5 | 5 | 5 | 5 | 5 | 3 | 3 | 4 |
| 14 | 20 | 5 | 5 | 5 | 5 | 5 | 5 | 5 | 4 | 4 | 4 |
| | 10 | 5 | 5 | 5 | 5 | 4 | 4 | 5 | 4 | 3 | 4 |
| 15 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 4 |
| 16 | 40 | 5 | 5 | 5 | 5 | 5 | 5 | 5 | 4 | 4 | 4 |
| | 20 | 5 | 5 | 5 | 5 | 5 | 4 | 5 | 3 | 4 | 3 |
| 17 | 20 | 5 | 5 | 5 | 5 | 5 | 5 | 5 | 4 | 4 | 5 |
| | 10 | 5 | 5 | 5 | 5 | 5 | 5 | 5 | 3 | 4 | 3 |
| 18 | 20 | 5 | 5 | 5 | 5 | 5 | 5 | 5 | 4 | 4 | 4 |
| | 10 | 5 | 5 | 5 | 5 | 5 | 5 | 5 | 4 | 3 | 4 |
| 19 | 20 | 5 | 5 | 5 | 5 | 5 | 5 | 5 | 4 | 5 | 5 |
| | 10 | 5 | 5 | 5 | 5 | 5 | 5 | 5 | 4 | 3 | 4 |
| 21 | 20 | 5 | 5 | 5 | 5 | 5 | 5 | 5 | 4 | 5 | 5 |
| | 10 | 5 | 5 | 5 | 5 | 5 | 5 | 5 | 3 | 3 | 4 |
| 24 | 20 | 5 | 5 | 5 | 5 | 5 | 5 | 5 | 4 | 4 | 5 |
| | 10 | 5 | 5 | 5 | 5 | 5 | 5 | 5 | 4 | 4 | 3 |
| 25 | 20 | 5 | 5 | 5 | 5 | 5 | 5 | 5 | 4 | 5 | 4 |
| | 10 | 5 | 5 | 5 | 5 | 5 | 5 | 5 | 4 | 3 | 4 |
| 27 | 20 | 5 | 5 | 5 | 5 | 5 | 5 | 5 | 5 | 4 | 5 |
| | 10 | 5 | 5 | 5 | 5 | 5 | 5 | 5 | 3 | 3 | 4 |
| 28 | 20 | 5 | 5 | 5 | 5 | 5 | 5 | 5 | 4 | 4 | 4 |
| | 10 | 5 | 5 | 5 | 5 | 5 | 5 | 5 | 3 | 4 | 3 |
| 31 | 20 | 5 | 5 | 5 | 5 | 5 | 5 | 5 | 5 | 4 | 4 |
| | 10 | 5 | 5 | 5 | 5 | 5 | 5 | 5 | 4 | 4 | 3 |
| 32 | 20 | 5 | 5 | 5 | 5 | 5 | 5 | 5 | 4 | 4 | 3 |
| | 10 | 5 | 5 | 5 | 4 | 5 | 4 | 5 | 3 | 3 | 2 |
| 33 | 20 | 5 | 5 | 5 | 5 | 5 | 5 | 5 | 4 | 4 | 5 |
| | 10 | 5 | 5 | 5 | 5 | 5 | 5 | 5 | 2 | 3 | 3 |
| 35 | 20 | 5 | 5 | 5 | 5 | 5 | 5 | 5 | 4 | 4 | 5 |
| | 10 | 5 | 5 | 5 | 5 | 5 | 5 | 5 | 3 | 4 | 3 |
| 36 | 20 | 5 | 5 | 5 | 5 | 5 | 5 | 5 | 5 | 4 | 4 |
| | 10 | 5 | 5 | 5 | 5 | 5 | 5 | 5 | 4 | 3 | 3 |
| 37 | 20 | 5 | 5 | 5 | 5 | 5 | 5 | 5 | 4 | 3 | 4 |
| | 10 | 5 | 5 | 5 | 5 | 5 | 5 | 5 | 2 | 2 | 3 |
| 38 | 20 | 5 | 5 | 5 | 5 | 5 | 5 | 5 | 4 | 3 | 4 |
| | 10 | 5 | 5 | 5 | 5 | 5 | 5 | 5 | 3 | 2 | 2 |
| 39 | 10 | 5 | 5 | 5 | 5 | 5 | 5 | 5 | 4 | 5 | 5 |
| | 5 | 5 | 5 | 5 | 5 | 5 | 5 | 5 | 3 | 4 | 3 |
| 40 | 20 | 5 | 5 | 5 | 5 | 5 | 5 | 5 | 3 | 4 | 4 |
| | 10 | 5 | 5 | 5 | 5 | 4 | 4 | 5 | 2 | 3 | 2 |
| 41 | 10 | 5 | 5 | 5 | 5 | 5 | 5 | 5 | 4 | 4 | 5 |
| | 5 | 5 | 5 | 5 | 5 | 5 | 5 | 5 | 3 | 3 | 4 |
| 42 | 20 | 5 | 5 | 5 | 5 | 5 | 5 | 5 | 3 | 3 | 4 |
| | 10 | 5 | 5 | 5 | 4 | 5 | 4 | 5 | 2 | 2 | 2 |
| 43 | 20 | 5 | 5 | 5 | 5 | 5 | 5 | 5 | 4 | 5 | 6 |
| | 10 | 5 | 5 | 5 | 5 | 5 | 5 | 5 | 3 | 4 | 3 |
| 45 | 40 | 5 | 5 | 5 | 5 | 5 | 5 | 5 | 3 | 4 | 3 |
| | 20 | 5 | 5 | 5 | 5 | 5 | 4 | 4 | 2 | 3 | 2 |
| 47 | 40 | 5 | 5 | 5 | 5 | 5 | 5 | 5 | 3 | 4 | 3 |
| | 20 | 5 | 5 | 5 | 4 | 5 | 3 | 4 | 1 | 2 | 2 |
| 48 | 40 | 5 | 5 | 5 | 5 | 5 | 5 | 5 | 3 | 4 | 4 |
| | 20 | 5 | 5 | 5 | 5 | 5 | 4 | 5 | 2 | 3 | 3 |
| 49 | 20 | 5 | 5 | 5 | 5 | 5 | 5 | 5 | 4 | 3 | 4 |
| | 10 | 5 | 5 | 5 | 5 | 4 | 4 | 5 | 2 | 2 | 3 |
| 51 | 40 | 5 | 5 | 5 | 5 | 5 | 5 | 5 | 3 | 4 | 4 |
| | 20 | 5 | 5 | 5 | 5 | 4 | 3 | 5 | 2 | 3 | 2 |
| 55 | 40 | 5 | 5 | 5 | 5 | 5 | 5 | 5 | 2 | 4 | 4 |
| | 20 | 5 | 5 | 5 | 4 | 5 | 3 | 4 | 1 | 2 | 3 |
| 56 | 20 | 5 | 5 | 5 | 5 | 5 | 5 | 5 | 3 | 3 | 4 |
| | 10 | 5 | 5 | 5 | 5 | 5 | 4 | 5 | 3 | 2 | 3 |
| 57 | 40 | 5 | 5 | 5 | 5 | 5 | 4 | 5 | 3 | 3 | 4 |
| | 20 | 5 | 5 | 5 | 5 | 4 | 4 | 5 | 2 | 1 | 2 |
| Chloroxuron | 20 | 5 | 5 | 5 | 5 | 5 | 5 | 5 | 4 | 4 | 4 |
| | 10 | 5 | 5 | 5 | 5 | 5 | 5 | 5 | 3 | 3 | 4 |
| Fluometuron | 20 | 5 | 5 | 5 | 5 | 5 | 5 | 5 | 4 | 3 | 4 |
| | 10 | 5 | 5 | 3 | 4 | 3 | 4 | 3 | 4 | 2 | 3 |

TABLE 1-continued

| Compound No. | Dosage (weight of active ingredient, g/are) | Herbicidal activity | | | | | | | | | |
|---|---|---|---|---|---|---|---|---|---|---|---|
| | | Redroot pigweed | Common lambs-quarters | Radish | Sun-flower | Cock-lebur | Tall morning-glory | Black night-shade | Large crab-grass | Barn-yard-grass | Green foxtail |
| Control (a) | 20 | 4 | 5 | 4 | 5 | 4 | 3 | 5 | 3 | 2 | 3 |
| | 10 | 4 | 5 | 4 | 5 | 3 | 1 | 4 | 1 | 2 | 2 |

EXAMPLE B (SELECTIVITY TO CROP PLANTS BY POST-EMERGENCE TREATMENT)

Wagner's pots (1/5000 are) were each filled with upland soil, and the seeds of soybean, cotton, sugarbeet, corn, wheat and rice plant were separately sowed in the pots and grown for 2 to 3 weeks in a greenhouse. Thereafter, a required amount of the test compound was sprayed to the foliage of the test plants over the top by means of a small hand sprayer. After the spraying, the test plants were grown for further 3 weeks in the greenhouse, and the phytotoxicity to each plant was examined. In the above foliar application, the test compounds were each formulated into an emulsifiable concentrate and dispersed in water for application at a volume of 5 liters per are with addition of a wetting agent. At this foliar application, soybean was in the first trifoliate leaf stage, cotton in 1-leaf stage, sugarbeet in 2-leaf stage, corn in 2-leaf stage, wheat in 2-leaf stage and rice plant in 3-leaf stage.

The results are shown in Table 2.

TABLE 2

| Compound No. | Dosage (weight of active ingredient, g/are) | Phytotoxicity | | | | | |
|---|---|---|---|---|---|---|---|
| | | Soy-bean | Cotton | Sugar-beet | Corn | Wheat | Rice plant |
| 1 | 20 | — | — | — | 1 | — | 0 |
| | 10 | — | — | — | 0 | — | 0 |
| 3 | 20 | 0 | — | — | — | — | — |
| | 10 | 0 | — | — | — | — | — |
| 4 | 20 | 0 | 0 | — | — | — | — |
| | 10 | 0 | 0 | — | — | — | — |
| 5 | 20 | 1 | — | 0 | — | 0 | — |
| | 10 | 0 | — | 0 | — | 0 | — |
| 7 | 20 | — | 1 | — | — | — | 0 |
| | 10 | — | 0 | — | — | — | 0 |
| 9 | 20 | 0 | — | — | — | — | 0 |
| | 10 | 0 | — | — | — | — | 0 |
| 15 | 20 | — | — | — | 1 | 1 | — |
| | 10 | — | — | — | 0 | 0 | — |
| 17 | 20 | 0 | — | — | — | — | — |
| | 10 | 0 | — | — | — | — | — |
| 19 | 20 | — | — | 0 | — | 0 | 0 |
| | 10 | — | — | 0 | — | 0 | 0 |
| 24 | 20 | 0 | — | 1 | — | — | 0 |
| | 10 | 0 | — | 0 | — | — | 0 |
| 28 | 20 | — | — | 0 | — | — | — |
| | 10 | — | — | 0 | — | — | — |
| 31 | 20 | — | — | 1 | — | 0 | 0 |
| | 10 | — | — | 1 | — | 0 | 0 |
| 33 | 20 | — | — | 1 | — | — | — |
| | 10 | — | — | 0 | — | — | — |
| 35 | 20 | — | — | 1 | 1 | 1 | — |
| | 10 | — | — | 0 | 0 | 0 | — |
| 36 | 20 | — | — | — | — | 0 | — |
| | 10 | — | — | — | — | 0 | — |
| 38 | 20 | — | — | 0 | — | 1 | — |
| | 10 | — | — | 0 | — | 0 | — |
| 39 | 10 | 1 | — | — | 0 | 0 | — |
| | 5 | 0 | — | 1 | 0 | 0 | — |
| 41 | 10 | — | — | 1 | — | 1 | — |
| | 5 | — | — | 1 | — | 0 | — |
| 43 | 20 | — | — | 1 | 1 | 0 | — |
| | 10 | — | — | 0 | 0 | 0 | — |
| 49 | 20 | 1 | — | — | 0 | 1 | — |
| | 10 | 0 | — | — | 0 | 0 | — |
| 56 | 20 | — | — | — | 0 | 0 | — |
| | 10 | — | — | — | 0 | 0 | — |
| Chloro-xuron | 20 | 3 | 5 | 5 | 4 | 4 | 4 |
| | 10 | 2 | 5 | 5 | 4 | 3 | 2 |
| Fluo-meturon | 20 | 4 | 2 | 5 | 3 | 4 | 4 |
| | 10 | 3 | 1 | 5 | 2 | 3 | 2 |
| Control (a) | 20 | 3 | 5 | 5 | 4 | 3 | 3 |
| | 10 | 2 | 3 | 5 | 2 | 2 | 2 |

EXAMPLE C (PRE-EMERGENCE APPLICATION TEST)

Plastic trays (35 cm×25 cm×10 cm (high)) were filled with upland field soil, and the weeds of redroot pigweed, common lambsquarters, radish, common purslane, large crabgrass, soybean, cotton, sugarbeet, corn, wheat and rice plants were separately sowed in the trays. The required amount of the test compound was sprayed to the whole surfaces of the field soil over the top by means of a small hand sprayer. In the application, the test compounds were each formulated into a wettable powder and the required amount of the wettable powder was dispersed in water for application at a spray volume of 5 liters per are. After the spraying, the test plants were grown for 20 days in the greenhouse, and the phytotoxicity and the herbicidal activity were examined according to the same criteria as shown above. The results are shown in Table 3.

TABLE 3

| Compound No. | Dosage (weight of active ingredient, g/are) | Phytotoxicity | | | | | | Herbicidal activity | | | | |
|---|---|---|---|---|---|---|---|---|---|---|---|---|
| | | Soybean | Cotton | Subar-beet | Corn | Wheat | Rice plant | Redroot pigweed | Common lambs-quarters | Radish | Common purs-lane | Large crabgrass |
| 1 | 50 | 0 | 0 | 1 | 0 | 0 | 0 | 5 | 5 | 5 | 5 | 5 |
| | 30 | 0 | 0 | 1 | 0 | 0 | 0 | 5 | 5 | 5 | 5 | 4 |
| 3 | 50 | 0 | 0 | 0 | 0 | 0 | 0 | 5 | 5 | 5 | 5 | 4 |
| | 30 | 0 | 0 | 0 | 0 | 0 | 0 | 5 | 5 | 5 | 5 | 4 |
| 4 | 50 | 0 | 0 | 0 | 0 | 0 | 0 | 5 | 5 | 5 | 5 | 4 |
| | 30 | 0 | 0 | 0 | 0 | 0 | 0 | 5 | 5 | 5 | 5 | 4 |

TABLE 3-continued

| Compound No. | Dosage (weight of active ingredient, g/are) | Phytotoxicity | | | | | | Herbicidal activity | | | | |
|---|---|---|---|---|---|---|---|---|---|---|---|---|
| | | Soybean | Cotton | Subarbeet | Corn | Wheat | Rice plant | Redroot pigweed | Common lambsquarters | Radish | Common purslane | Large crabgrass |
| 7 | 50 | 0 | 1 | 1 | 0 | 0 | 0 | 5 | 5 | 5 | 5 | 5 |
| | 30 | 0 | 0 | 0 | 0 | 0 | 0 | 5 | 5 | 5 | 5 | 4 |
| 14 | 50 | 0 | 0 | 0 | 0 | 0 | 0 | 5 | 5 | 5 | 5 | 4 |
| | 30 | 0 | 0 | 0 | 0 | 0 | 0 | 5 | 5 | 5 | 5 | 3 |
| 18 | 50 | 0 | 0 | 0 | 0 | 0 | 0 | 5 | 5 | 5 | 5 | 5 |
| | 30 | 0 | 0 | 0 | 0 | 0 | 0 | 5 | 5 | 5 | 5 | 4 |
| 19 | 50 | 0 | — | 0 | 0 | — | — | 5 | 5 | 5 | 5 | 4 |
| | 30 | 0 | — | 0 | 0 | — | — | 5 | 5 | 5 | 5 | 3 |
| 25 | 50 | 0 | 0 | 0 | 0 | 0 | 0 | 5 | 5 | 5 | 5 | 5 |
| | 30 | 0 | 0 | 0 | 0 | 0 | 0 | 5 | 5 | 5 | 5 | 5 |
| 28 | 50 | — | — | 0 | — | — | 0 | 5 | 5 | 5 | 5 | 3 |
| | 30 | — | — | 0 | — | — | 0 | 5 | 5 | 5 | 5 | 2 |
| 38 | 50 | 0 | — | 0 | — | 0 | — | 5 | 5 | 5 | 5 | 4 |
| | 30 | 0 | — | 0 | — | 0 | — | 5 | 5 | 5 | 5 | 3 |
| 39 | 50 | 0 | 0 | — | — | — | 0 | 5 | 5 | 5 | 5 | 4 |
| | 30 | 0 | 0 | — | — | — | 0 | 5 | 5 | 5 | 5 | 4 |
| 41 | 50 | 0 | — | — | 0 | — | — | 5 | 5 | 5 | 5 | 4 |
| | 30 | 0 | — | — | 0 | — | — | 5 | 5 | 5 | 5 | 3 |
| Chloramben | 20 | 0 | 4 | — | 4 | 2 | 2 | 4 | 5 | 3 | 5 | 5 |
| | 10 | 0 | 4 | — | 3 | 1 | 1 | 4 | 3 | 1 | 5 | 4 |
| Chloroxuron | 40 | 0 | — | 4 | — | — | 1 | 4 | 4 | 3 | 4 | 1 |
| | 20 | 0 | — | 3 | — | — | 0 | 4 | 3 | 2 | 3 | 0 |

EXAMPLE D (PADDY RICE TEST)

Wagner's pots (1/5000 are) were each filled with 1.5 kg of paddy field soil containing the seeds of weeds and kept under flooded conditions. The seedlings of rice plant at a 3-leaf stage were transplanted thereto, and after the seeds of barnyard grass were sowed therein, the seedlings were grown for 5 days in a greenhouse. Thereafter, the required amount of the wettable powder of each test compound was diluted with water and applied to the soil under flooded conditions. Twenty days after the application, the evaluation of the herbicidal activity and the phytotoxicity was made on the rice plants and barnyard grass as well as broadleaved weeds (e.g. pickerel weed (*Monochoria vaginalis*), false pimpernel (*Lindernia pyxidaria*), toothcup (*Rotala inidca*)) and Hotarui (*Scirpus hotarui*). The results are shown in Table 4.

TABLE 4

| Compound No. | Dosage (weight of active ingredient, g/are) | Phytotoxicity Rice plant | Herbicidal activity | | |
|---|---|---|---|---|---|
| | | | Barn yardgrass | Broadleaved weeds | *Scirpus hotarui* |
| 1 | 20 | 0 | 5 | 5 | 5 |
| | 10 | 0 | 4 | 5 | 5 |
| 2 | 20 | 0 | 4 | 5 | 5 |
| | 10 | 0 | 4 | 5 | 3 |
| 3 | 20 | 0 | 4 | 5 | 5 |
| | 10 | 0 | 3 | 5 | 3 |
| 5 | 20 | 0 | 4 | 5 | 5 |
| | 10 | 0 | 4 | 5 | 5 |
| 6 | 20 | 0 | 4 | 5 | 5 |
| | 10 | 0 | 3 | 5 | 4 |
| 7 | 20 | 0 | 5 | 5 | 5 |
| | 10 | 0 | 5 | 5 | 5 |
| 8 | 20 | 0 | 5 | 5 | 5 |
| | 10 | 0 | 4 | 5 | 5 |
| 9 | 20 | 0 | 4 | 5 | 5 |
| | 10 | 0 | 4 | 5 | 5 |
| 10 | 20 | 0 | 5 | 5 | 5 |
| | 10 | 0 | 3 | 5 | 4 |
| 12 | 20 | 0 | 4 | 5 | 5 |
| | 10 | 0 | 3 | 5 | 5 |
| 13 | 20 | 0 | 4 | 5 | 5 |
| | 10 | 0 | 3 | 5 | 3 |
| 15 | 20 | 0 | 5 | 5 | 5 |
| | 10 | 0 | 5 | 5 | 5 |
| 18 | 20 | 0 | 5 | 5 | 5 |
| | 10 | 0 | 4 | 5 | 5 |
| 19 | 20 | 0 | 4 | 5 | 4 |
| | 10 | 0 | 3 | 5 | 3 |
| 20 | 20 | 0 | 4 | 5 | 5 |
| | 10 | 0 | 3 | 5 | 4 |
| 21 | 20 | 0 | 5 | 5 | 5 |
| | 10 | 0 | 4 | 5 | 5 |
| 22 | 20 | 0 | 4 | 5 | 5 |
| | 10 | 0 | 3 | 5 | 3 |
| 23 | 20 | 0 | 4 | 5 | 4 |
| | 10 | 0 | 3 | 4 | 3 |
| 24 | 20 | 0 | 5 | 5 | 5 |
| | 10 | 0 | 4 | 5 | 5 |
| 25 | 20 | 0 | 5 | 5 | 5 |
| | 10 | 0 | 4 | 5 | 5 |
| 26 | 20 | 0 | 5 | 5 | 5 |
| | 10 | 0 | 3 | 5 | 5 |
| 28 | 20 | 0 | 3 | 5 | 5 |
| | 10 | 0 | 2 | 5 | 4 |
| 29 | 20 | 0 | 4 | 5 | 5 |
| | 10 | 0 | 3 | 5 | 5 |
| 30 | 20 | 0 | 5 | 5 | 5 |
| | 10 | 0 | 3 | 5 | 3 |
| 31 | 20 | 0 | 4 | 5 | 5 |
| | 10 | 0 | 4 | 5 | 5 |
| 33 | 20 | 0 | 5 | 5 | 5 |
| | 10 | 0 | 4 | 5 | 5 |
| 34 | 20 | 0 | 4 | 5 | 5 |
| | 10 | 0 | 3 | 5 | 4 |
| 38 | 20 | 0 | 4 | 5 | 5 |
| | 10 | 0 | 2 | 5 | 5 |
| 39 | 20 | 0 | 5 | 5 | 5 |
| | 10 | 0 | 4 | 5 | 5 |
| 41 | 20 | 1 | 5 | 5 | 5 |
| | 10 | 0 | 5 | 5 | 5 |
| 44 | 20 | 0 | 4 | 5 | 5 |
| | 10 | 0 | 2 | 5 | 3 |
| 46 | 20 | 0 | 4 | 5 | 5 |
| | 10 | 0 | 3 | 5 | 3 |
| 53 | 20 | 0 | 4 | 5 | 4 |
| | 10 | 0 | 3 | 5 | 3 |
| MCP | 20 | 3 | 4 | 5 | 4 |

TABLE 4-continued

| Compound No. | Dosage (weight of active ingredient, g/are) | Phytotoxicity Rice plant | Herbicidal activity | | |
|---|---|---|---|---|---|
| | | | Barnyard-grass | Broad-leaved weeds | *Scirpus hotarui* |
| | 10 | 2 | 3 | 5 | 2 |

What is claimed is:

1. A compound of the formula:

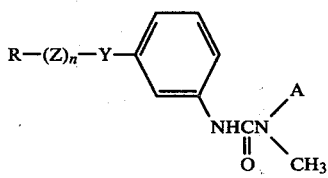

wherein R is a $C_4$-$C_{10}$ cycloalkyl group, a $C_4$-$C_{10}$ cycloalkenyl group, a $C_4$-$C_{10}$ cycloalkyl group condensed with a benzene ring or substituted with at least one $C_1$-$C_4$ alkyl group or a $C_4$-$C_{10}$ cycloalkenyl group condensed with a benzene ring or substituted with a $C_1$-$C_4$ alkyl group, Z is a $C_1$-$C_4$ alkylene group which may have an atom of oxygen and/or sulfur at the terminal of the carbon chain, Y is an oxygen atom or a sulfur atom, A is a hydrogen atom, a methyl group or a methoxy group and n is an integer of 0 or 1, with the proviso that in the chain consisting of —$(Z)_n$—y—, oxygen and/or sulfur atoms are not present in succession.

2. The compound according to claim 1, wherein R is a $C_4$-$C_{10}$ cycloalkyl group, Z is a $C_1$-$C_4$ alkylene group or a $C_1$-$C_4$ alkylene group having an oxygen atom at the terminal of the carbon chain, Y is an oxygen atom, A is a methyl group or a methoxy group and n is an integer of 0 or 1 with the proviso that in the chain consisting of —$(Z)_n$—Y—, oxygen atoms are not present in succession.

3. The compound according to claim 1, wherein R is a $C_4$-$C_{10}$ cycloalkyl group condensed with a benzene ring or substituted with at least one $C_1$-$C_4$ alkyl group, Z is a $C_1$-$C_4$ alkylene group or a $C_1$-$C_4$ alkylene group having an oxygen atom at the terminal of the carbon chain, Y is an oxygen atom, A is a methyl group or a methoxy group and n is an integer of 0 or 1 with the proviso that in the chain consisting of —$(Z)_n$—Y—, oxygen atoms are not present in succession.

4. The compound according to claim 2, which is N'-3-[2-(1-adamantane)ethoxy]phenyl-N-methoxy-N-methylurea.

5. The compound according to claim 2, which is N'-3-[3(or 4)-(tricyclo[5.2.1.0$^{2,6}$]decyl)methoxy]phenyl-N-methoxy-N-methylurea.

6. The compound according to claim 3, which is N'-3-[2-(3-methylcyclohexyl)ethoxy]phenyl-N,N-dimethylurea.

7. A herbicidal composition comprising as an active ingredient at least one of the compounds of the formula:

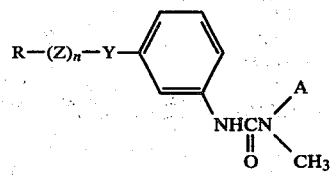

wherein R is a $C_4$-$C_{10}$ cycloalkyl group, a $C_4$-$C_{10}$ cycloalkenyl group, a $C_4$-$C_{10}$ cycloalkyl group condensed with a benzene ring or substituted with at least one $C_1$-$C_4$ alkyl group or a $C_4$-$C_{10}$ cycloalkenyl group condensed with a benzene ring or substituted with a $C_1$-$C_4$ alkyl group, Z is a $C_1$-$C_4$ alkylene group which may have an atom of oxygen and/or sulfur at the terminal of the carbon chain, Y is an oxygen atom or a sulfur atom, A is a hydrogen atom, a methyl group or a methoxy group and n is an integer of 0 or 1 with the proviso that in the chain consisting of —$(Z)_n$—Y—, oxygen and/or sulfur atoms are not present in succession, and an inert carrier.

8. The composition according to claim 7, wherein the concentration of the active ingredient is from about 1 to 95% by weight.

9. A method for controlling weeds which comprises applying at least one of the compounds of the formula:

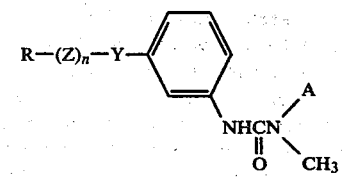

wherein R is a $C_4$-$C_{10}$ cycloalkyl group, a $C_4$-$C_{10}$ cycloalkenyl group, a $C_4$-$C_{10}$ cycloalkyl group condensed with a benzene ring or substituted with at least one $C_1$-$C_4$ alkyl group or a $C_4$-$C_{10}$ cycloalkenyl group condensed with a benzene ring or substituted with a $C_1$-$C_4$ alkyl group, Z is a $C_1$-$C_4$ alkylene group which may have an atom of oxygen and/or sulfur at the terminal of the carbon chain, Y is an oxygen atom or a sulfur atom, A is a hydrogen atom, a methyl group or a methoxy group and n is an integer of 0 or 1 with the proviso that in the chain consisting of —$(Z)_n$—Y—, oxygen and/or sulfur atoms are not present in succession, to the area where the weeds grow.

10. A method of selectively combating weeds in cultivation of sugarbeet, soybean, cotton, rice, wheat or corn, which comprises applying a herbicidally effective amount of the compound of the formula:

wherein R is a $C_4$-$C_{10}$ cycloalkyl group, a $C_4$-$C_{10}$ cycloalkenyl group, a $C_4$-$C_{10}$ cycloalkyl group condensed with a benzene ring or substituted with at least one $C_1$-$C_4$ alkyl group or a $C_4$-$C_{10}$ cycloalkenyl group condensed with a benzene ring or substituted with a $C_1$-$C_4$ alkyl group, Z is a $C_1$-$C_4$ alkylene group which may have an atom of oxygen and/or sulfur at the terminal of the carbon chain, Y is an oxygen atom or a sulfur atom, A is a hydrogen atom, a methyl group or a methoxy group and n is an integer of 0 or 1 with the proviso that in the chain consisting of —$(Z)_n$—Y—, oxygen and/or sulfur atoms are not present in succession, to the area where sugarbeet, soybean, cotton, rice, wheat or corn crop is cultivated.

11. A method of selectively combating weeds in the cultivation of sugarbeet which comprises applying a herbicidally effective amount of the composition of claim 7 to the area where the sugarbeet is cultivated.

* * * * *